United States Patent

Fischer et al.

Patent Number: 6,093,857

Date of Patent: *Jul. 25, 2000

[54] PREPARATION OF CYCLOPENTANOLS

[75] Inventors: Rolf Fischer, Heidelberg; Rolf Pinkos, Bad Dürkheim; Norbert Rieber, Mannheim; Michael Schulz; Joaquim Henrique Teles, both of Ludwigshafen, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/928,524

[22] Filed: Sep. 12, 1997

[30] Foreign Application Priority Data

Sep. 13, 1996 [DE] Germany .................... 196 37 429

[51] Int. Cl.⁷ .................................................. C07C 35/06
[52] U.S. Cl. ............................................ 568/838; 560/241
[58] Field of Search ........................... 568/838, 822; 558/260; 560/129, 247, 231, 241

[56] References Cited

U.S. PATENT DOCUMENTS

| | | | |
|---|---|---|---|
| 2,444,129 | 6/1948 | Bearse | 560/247 |
| 2,534,304 | 12/1950 | Serniuk | 560/247 |
| 3,527,816 | 9/1970 | Norell et al. | |
| 3,644,497 | 2/1972 | Mesich | 560/247 |
| 4,365,083 | 12/1982 | Young | 560/247 |
| 4,365,084 | 12/1982 | Young | 560/247 |
| 4,430,508 | 2/1984 | Sprecker | 560/231 |
| 4,506,105 | 3/1985 | Kaufhold | 560/231 |
| 4,927,954 | 5/1990 | Knopf | 560/247 |
| 5,475,158 | 12/1995 | Krug et al. | 568/835 |

FOREIGN PATENT DOCUMENTS

| | | |
|---|---|---|
| 2559480 | 1/1977 | Germany . |
| 4029485 | 3/1992 | Germany . |
| 1153468 | 5/1969 | United Kingdom . |

OTHER PUBLICATIONS

Guenzet, Tetrahedron, vol. 35, pp. 473–480, 1979.
Dorris et al., J.A. Nieuwland, J. Am. Chem. Soc., 56 (1934) pp. 2689 to 2690.
Wunderly et al., J. Am. Chem. Soc., 59, (1973) pp. 1010 to 1011.
Peterson et al., J. Org. Chem. 29 (1964) pp. 2322 to 2325.

*Primary Examiner*—Michael L. Shippen
*Attorney, Agent, or Firm*—Keil & Weinkauf

[57] ABSTRACT

A process for preparing cyclopentyl formates of the formula (II)

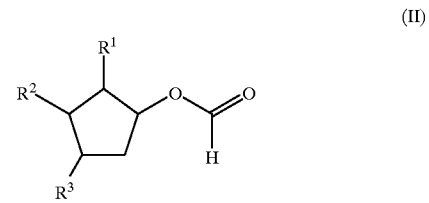

by reacting cyclopentenes of the formula (I)

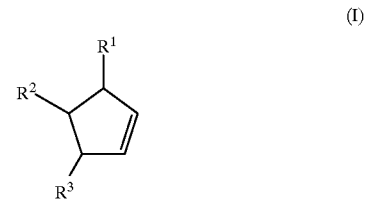

where $R^1$, $R^2$ and $R^3$, independently of one another, are hydrogen atoms or $C_{1-8}$-alkyl, with formic acid in the presence of an acid catalyst.

10 Claims, No Drawings

PREPARATION OF CYCLOPENTANOLS

The invention relates to a process for preparing substituted or unsubstituted cyclopentanols. The invention further relates to a process for preparing substituted or unsubstituted cyclopentyl formates from which the cyclopentanols are prepared.

The preparation of cyclopentyl compounds as a rule makes use of cyclopentanone which can be obtained by Ruzicka cyclization of adipic acid or adipic acid esters. The cyclopentanone thus obtained is then employed in further reactions. The synthesis has the drawback that more than 40% of the starting material is lost as water and carbon dioxide.

There is therefore a need for other processes for preparing cyclopentyl compounds, making better use of the starting materials.

Processes for preparing specific cyclic and acyclic alkanols are known. U.S. Pat. No. 3,527,816 discloses a process for preparing olefinic alcohols, in which triolefins containing two substituted or unsubstituted cyclohexene rings linked via an ethene unit are reacted with aliphatic carboxylic acids such as formic acid and the resulting formic acid esters are cleaved to give the corresponding alcohols.

H. L. Wunderly, F. J. Sowa, J. Am. Chem. Soc., 59 (1973), pp. 1010 to 1011 disclose the addition of acetic acid to cyclohexene in the presence of a compound of acetic acid and boron fluoride, the amount of boron fluoride used significantly affecting the amount of ester obtained. In this process, high boron fluoride concentrations and long reaction times of from 50 to 220 hours are employed. The reaction is accompanied by polymerization of cyclohexene as a side reaction.

T. B. Dorris, F. J. Sowa, J. A. Nieuwland, J. Am. Chem. Soc., 56 (1934), pp. 2689 to 2690 disclose the condensation of propylene with acetic acid, mono-, di- and trichloroacetic acid and benzoic acids, which leads to the corresponding isopropyl esters.

P. E. Peterson, E. V. P. Tao, J. Org. Chem., 29 (1964), pp. 2322 to 2325 disclose the addition of acetic acid, formic acid and trifluoroacetic acid to branched alkenes. These are alkenes having three alkyl substituents on the double bond which react with the acids in an equilibrium reaction. The yields of esters and alcohols are correspondingly low. The yield for 1-methylcyclopentanol is about 50%.

The GB patent 1,153,468 discloses the preparation of cyclooctyl compounds, in particular cyclooctyl formate and cyclooctanol, and of cyclooctanone, cyclooctene being reacted with formic acid to give cyclooctyl formate which is then cleaved to produce the alcohol.

Refinery or cracker cuts, especially $C_5$ cuts, contain cyclopentene as a minor component. The components can be enriched by distillation. The cyclopentene thus obtained has hitherto been used, as the $C_5$ cut, as an additive for gasolines.

It is an object of the present invention to provide a process for preparing cyclopentyl formates and cyclopentanols.

It is a further object of the invention to provide an economical process for producing cyclopentyl formates and cyclopentanols, which does not give rise to any coupling products and ensures efficient utilization of the starting materials. At the same time the reaction time is to be short and the use of large amounts of boron trifluoride and the formation of by-products are to be avoided.

We have found that this object is achieved by a process for preparing cyclopentyl formates of the formula (II)

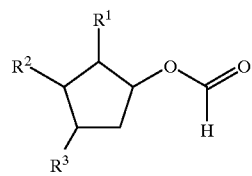

(II)

by reacting cyclopentenes of the formula (I)

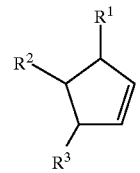

(I)

where $R^1$, $R^2$ and $R^3$, independently of one another, are hydrogen atoms or $C_{1-8}$-, preferably $C_{1-4}$-alkyl, with formic acid in the presence of an acid catalyst.

These objects are further achieved by a process for preparing cyclopentanols of the formula (III)

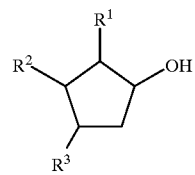

(III)

by reacting the cyclopentyl formates obtained with a compound of the formula $R^4{}_nXH$, where X is nitrogen and n has the value 2 or X is oxygen and n has the value 1 and $R^4$, possibly independently of each other, is hydrogen, a linear or branched $C_{1-12}$-alkyl or a $C_{7-12}$-aralkyl.

We have found, according to the invention, that cyclopentenes can be reacted, as described above, to produce cyclopentyl formates and cyclopentanols. Virtually no polymer formation is observed in the process. Moreover, the reaction gives high yields in a short time, the use of large amounts of boron trifluoride being unnecessary. In contrast to the use of acetic acid and cyclohexene, employed in analogy to Wunderly and Sowa, the reaction according to the invention of cyclopentene and formic acid gives high conversion in a short time. It was found, in particular, that it is possible to use $C_5$ streams from a (steam) cracker or a refinery. In contrast, the use of a $C_6$ stream of cyclohexene and cyclohexane results in very low conversions when reacted with acetic acid.

Refining or cracking, especially steam cracking of crude oil or crude oil fractions produces various cuts or streams which predominantly contain hydrocarbons having a specific number of carbon atoms. Thus $C_5$ cuts can be obtained from refinery or cracker streams. These $C_5$ cuts contain a cyclopentene fraction as well as, mainly, n-pentane, pentane isomers and pentene isomers and also cyclopentane. A typical $C_5$ stream which can be obtained when steam cracker mixtures are processed in a side stream of the $C_5$ distillation column has the following composition:

| NAME | Bp./° C. | Content/wt % |
|---|---|---|
| 2-Methylbutane | 30 | 8 |
| 2-Methyl-1-butene | 31 | 2 |
| n-Pentane | 35–36 | 34 |
| 2-Methyl-2-butene | 35–38 | 13 |
| cis-2-Pentene | 37–38 | 3 |
| trans-2-Pentene | 37 | 9 |
| Cyclopentene | 44–46 | 17 |
| Cyclopentane | 50 | 13 |
| 2,2-Dimethylbutane | 50 | 1 |

As the main components the mixture contains n-pentane, 2-methyl-2-butene, cyclopentane and cyclopentene. This mixture can be separated further by distillation, the low-boiling components being distilled off, preferably to such an extent that the content of 2-pentenes in the mixture remaining as the bottom product is at most 10, preferably at most 3, especially at most 1 wt %, the bottom product mixture having the following composition, for example:

| NAME | Bp./° C. | Content/wt % |
|---|---|---|
| 2-Methylbutane | 30 | <0.01 |
| 2-Methyl-1-butene | 31 | <0.01 |
| n-Pentane | 35–36 | 1 |
| 2-Methyl-2-butene | 35–38 | 6 |
| cis-2-Pentene | 37–38 | 0.4 |
| trans-2-Pentene | 37 | 0.5 |
| Cyclopentene | 44–46 | 49 |
| Cyclopentane | 50 | 39 |
| 2,2-Dimethylbutane | 50 | 3 |

The bottom product therefore mainly comprises cyclopentene and cyclopentane.

The novel process can make use of pure cyclopentene which, for example, can be extracted from the abovementioned bottom product. According to one embodiment of the invention, the cyclopentene is used in the form of a $C_5$ stream from a (steam) cracker or a refinery, the content of cyclopentene(s) preferably being from 20 to 100, especially from 40 to 80 wt %, while the content of 2-pentenes should preferably be at most 3, especially at most 1 wt %.

According to a preferred embodiment of the invention, a mixture of a $C_5$ stream from a (steam) cracker or a refinery is used, from which more volatile components, especially those having a boiling point in the range of from 30 to 40° C., have been largely removed by distillation. Such a mixture preferably has a cyclopentene(s) content of from 20 to 100, especially from 40 to 80 wt %. The 2-pentenes content is preferably at most 3, especially at most 1 wt %.

Noncyclic olefins which are mono-, di- or trisubstituted on the double bond, like those occurring eg. in the cracker or refinery cuts, can likewise react with formic acid to form alkyl formates. It may then be necessary for these undesired by-products to be separated, if cyclopentyl formate is to be obtained in as pure a form as possible.

The cyclopentene(s) can therefore be employed, according to the invention, in pure form or in the form of mixtures, with the option of the cyclopentenes content in a particular starting mixture being increased, if required, by lower-boiling components being distilled off or separated.

In a first step, the cyclopentenes or cyclopentene-containing hydrocarbon mixtures such as $C_5$ streams are reacted with formic acid to give the corresponding cyclopentyl formates. The cyclopentenes employed in the process have the structure shown in the following formula (I):

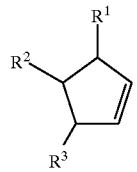

(I)

where $R^1$, $R^2$ and $R^3$, independently of one another, are hydrogen or $C_{1-8}$-, preferably $C_{1-4}$-alkyl, where the alkyl radicals may be straight-chain or branched. Particularly preferably, all the radicals are hydrogen or from 1 to 3 of the radicals are methyl, ethyl, n-propyl, isopropyl, n-butyl, isobutyl or t-butyl, the other radicals being hydrogen. Particularly preferably, all the radicals are hydrogen or from 1 to 3 of the radicals $R^1$, $R^2$ and $R^3$ are methyl, the other radicals being hydrogen. In particular, all the radicals $R^1$, $R^2$ and $R^3$ are hydrogen, ie. cyclopentene is employed.

In the description the term "cyclopentenes" relates to the cyclopentenes of the formula (I). Correspondingly the terms "cyclopentene formates" and "cyclopentanols" refer to the corresponding compounds of the formulae (II) and (III).

The cyclopentyl formates have the formula (II)

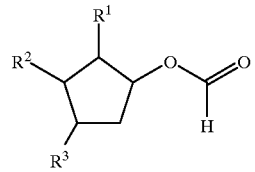

(II)

where the radicals have the previously stated meanings. The reaction takes place in the presence of a homogeneous or heterogeneous acid catalyst.

The acid catalyst employed can be any suitable substance which catalyzes the reaction of the cyclopentenes with formic acid, for example Lewis or Brönsted acids. According to one embodiment of the invention, the acid catalyst is selected from Lewis acids of the formulae $BX_3$, $AlX_3$, $SnX_4$, $FeX_3$, $MgX_2$ or $ZnX_2$, where X is a halide or the radical $C_6F_5$. The halides may, according to the invention, in particular comprise fluorine, chlorine, bromine and iodine as well as mixed halides therefrom.

According to one embodiment of the invention the metal halides are anhydrous.

Particular preference is give to the use of $BF_3$ and $ZnCl_2$. The Lewis acids may be employed in the form of adducts, for example with ethers or alcohols. Preference is given to the use of the alkyl ethers such as diethyl ether or alkanols such as methanol. Particular preference is given to the use of the $BF_3$-diethyl ether adduct $BF_3.OEt_2$.

It is also possible to employ, as catalysts metal complexes of the formula $(R_3P)MY$, where M is copper, silver or gold. Y is a halide, for example fluoride, chloride, bromide or iodide, nitrate, sulfate, carboxylate or tosylate. R is a $C_{1-12}$-, preferably $C_{1-4}$-, especially $C_1$-alkyl, $C_{6-12}$-, preferably $C_{6-8}$-aryl, $C_{1-12}$-O—, preferably $c_{1-4}$-O—, especially $C_1$-O- alkyl or $C_{6-12}$-O—, preferably $C_{6-8}$-O-aryl. Preferably the radical R is methyl and Y is iodide, examples of preferred compounds according to the invention being $(MeO)_3PCuI$ and $Me_3PAgI$.

It is also possible to employ, as heterogeneous catalysts, Lewis acid or Brönsted acid solids such as eg. acid zeolites or acid ion exchangers. An example of an acid ion exchanger is Amberlyst® XN 1010, produced by Rohm and Haas, an example of an acid zeolite being ZSM-11 (H form). The heterogeneous catalysts can be employed in any suitable form, for example as a powder or as granules, in suspension or as a fixed bed.

According to the invention the catalyst is employed in an amount of from 0.0001 to 25 mol %, preferably from 0.005 to 5 mol %, especially from 0.01 to 1 mol %, based on the total amount of cyclopentene.

Particularly preferably, $BF_3.OEt_2$ is employed in an amount of from 0.02 to 0.5 mol %.

The ratio of the amounts of formic acid to cyclopentene can likewise be varied over a wide range. According to one embodiment of the invention an excess of formic acid is employed, to ensure as complete a conversion of cyclopentene as possible. The molar ratio of formic acid to cyclopentene, according to one embodiment of the invention, is in the range from 0.1 to 25, preferably from 1 to 10, especially from 1.5 to 4.

The conversion can be carried out under customary temperatures and pressures.

According to one embodiment of the invention the reaction is carried out at from −80 to +200° C., preferably from 0° C. to 150° C., especially from 35° C. to 80° C. According to one embodiment the reaction is carried out at about 80° C. under the intrinsic pressure of the reactants.

The crude cyclopentyl formate obtained in the reaction can be purified by distillation. In the process, formic acid and any other hydrocarbons or formates which may be present are removed. If, for example, a mixture of a $C_5$ stream from a (steam) cracker or a refinery is used, the remaining hydrocarbons are distilled off after the reaction, according to one embodiment of the invention.

According to a further embodiment of the invention, if a mixture of a $C_5$ stream is used, the reaction mixture is extracted by means of the cyclopentane present in the mixture. Cyclopentane is well suited for this extraction, since the solubility of formic acid in cyclopentane is only 0.2 wt %. The solubility of formic acid in n-pentane, for example, is 1.7 wt % at room temperature. Thus a cyclopentyl formate low in formic acid can be obtained directly in the cyclopentane phase. The crude cyclopentyl formate thus obtained can be employed, without further purification, in the second reaction stage.

According to one embodiment of the invention the cyclopentane is removed from the crude cyclopentyl formate thus obtained, for example by means of distillation, only small amounts of formic acid dissolved in the cyclopentane having to be distilled off, so that corrosion problems in the distillation apparatus are avoided. The formic acid-rich phase resulting is from the extraction can be recycled directly into the reaction.

Likewise, the cyclopentane removed during the distillation can be recycled into the reaction or the extraction or can be discharged. In addition to the cyclopentane, which according to the invention is preferred for the extraction, it is also possible to use any other suitable extractant, those extractants being used preferentially which have a low solubility for formic acid.

The cyclopentyl formate obtained can be employed for a large number of chemical reactions.

According to one embodiment of the invention, the cyclopentyl formate formed is converted into cyclopentanol. The cyclopentyl formate can for example be hydrolyzed with aqueous alkali, in particular aqueous sodium hydroxide solution. This process consumes stoichiometric amounts of sodium hydroxide, and the resultant formic acid is produced in the form of sodium formate.

According to one embodiment of the invention, the cyclopentyl formates are reacted with a compound of the formula $R^4{}_nXH$, where X is nitrogen and n has the value 2 or X is oxygen and n has the value 1 and $R^4$, possibly independently of each other, is hydrogen, a linear or branched $C_{1-12}$-alkyl or a $C_{7-12}$-aralkyl.

Preferably, $R^4$ is hydrogen or methyl, especially hydrogen if X is nitrogen. $R^4$ is preferably $C_{1-4}$-alkyl such as methyl, ethyl, n-propyl, i-propyl, n-butyl, i-butyl, tert-butyl, preferably methyl, especially if X is oxygen.

The reaction with ammonia, which can be employed either as a gas or as an aqueous solution, or with amines produces formamides.

Preferred according to the invention is the reaction of the cyclopentyl formate with methanol, preferably in the presence of a transesterification catalyst. In the process, the cyclopentyl formate is converted into cyclopentanol and at the same time methanol into methyl formate. Possible catalysts for this reaction are, according to the invention, bases, acids or metal complexes such as, for example, titanates or dibutyltin dilaurate. Preference is given to the use of bases such as, in particular, sodium methylate as the catalyst.

The methyl formate produced during the reaction is readily separated from the reaction mixture by distillation. According to one embodiment of the invention, the methyl formate thus obtained is hydrolyzed, in the presence or absence of a basic catalyst, to formic acid and methanol, which are recycled into the synthesis, the formic acid preferably being recycled into the first reaction of cyclopentenes with formic acid, the methanol being recycled into the transesterification of the cyclopentyl formate.

With this embodiment of the invention the overall result for the two reaction steps is, as the net reaction, the addition of water to cyclopentene. No coupling product is formed in addition to the desired product.

The transesterification with methanol proceeds almost quantitatively, so that the reaction produces very pure cyclopentanol. The cyclopentanol can, according to one embodiment of the invention, be used directly in further chemical reactions, in which cyclopentanol is an intermediate for the synthesis of various cyclopentane derivatives. Known processes can be employed to prepare, for example, cyclopentanone, cyclopentylamine, cyclopentyl chloride and cyclopentyl bromide, as well as cyclopentyl chloroformate. If the cyclopentanol is required to be extremely pure, the cyclopentanol obtained can, for example, be further purified by distillation.

Especially if $C_5$ streams from a (steam) cracker or a refinery are used, possibly after more volatile components have been removed by distillation, cyclopentanols can be prepared very economically, since cyclopentane simultaneously present in the $C_5$ stream is used as the extractant and the chemical compounds used can be recycled into the reaction. Especially the methyl formate produced in the transesterification can be recycled into the formic acid synthesis or, after separate ester cleavage, can be recycled into the first or second reaction step.

The invention is illustrated below by way of examples.

EXAMPLES 1 to 7

Reaction of Cyclopentene with Formic Acid

Cyclopentene (96%, 35.4 g, 0.5 mol), formic acid (99%, 92 g, 2 mol) and the catalyst specified in the following table (5 mmol, 1 mol %) were introduced into a glass autoclave and heated with thorough stirring for three hours at 80° C. under intrinsic pressure. After the mixture had cooled, selectivity and conversion ratios were determined by quantitative gas chromatography. The results are summarized n the following table.

| EXAM-PLE | CATALYST | CYCLOPENTENE CONVERSION RATIO | SELEC-TIVITY % |
|---|---|---|---|
| 1 | without | 19 | 48 |
| 2 | $BF_3$—$OEt_2$ | 96 | >98 |
| 3 | $BF_3$—$OEt_2$ (0.1 mol %) | 92 | >98 |
| 4 | $ZnCl_2$ (anhydrous) | 85 | 59 |
| 5 | $(MeO)_3PCuI$ | 54 | 59 |
| 6 | $Me_3PAgI$ | 28 | 51 |
| 7 | $FeCl_3$ | 71 | >98 |

The results of the table show that cyclopentene can be converted into cyclopentyl formate with a high yield and high selectivity, particularly if a catalyst is used, especially $BF_3 \cdot OEt_2$.

EXAMPLES 8 and 9

Reaction of Cyclopentene with Formic Acid on Heterogeneous Catalysts

Cyclopentene (96%, 35.4 g, 0.5 mol), formic acid (99%, 92 g, 2 mol) and catalyst were introduced into a glass autoclave and heated with thorough stirring for 2 hours at 80° C. under intrinsic pressure. After the mixture had cooled, selectivity and conversion ratios were determined by quantitative gas chromatography. The results are summarized in the following table.

| EX-AM-PLE | CATALYST | Amount | CYCLOPENTENE CONVERSION RATIO | SELEC-TIVITY % |
|---|---|---|---|---|
| 8 | ZSM-11-zeolite (H form) | 25 g | 93 | >98 |
| 9 | Amberlyst XN 1010 ® (acid ion exchanger) | 25 g | 89 | >98 |

Amberlyst XN 1010 ® is produced by Rohm and Haas.

Comparative Example 1

For purposes of comparison, the starting materials cyclohexene and acetic acid, employed by Wunderly and Sowa in the prior art, were reacted in accordance with Example 2. To this end, cyclohexene (41 g, 0.05 mol), acetic acid (120 g, 2 mol) and $BF_3$ etherate (5 mmol) were introduced, similar to Example 2, into a glass autoclave and heated, with thorough stirring, for three hours at 80° C. under intrinsic pressure. After the mixture had cooled down, the selectivity and conversion ratios were determined by quantitative gas chromatography. The result was a cyclohexene conversion ratio of 12% with a selectivity of more than 98%.

EXAMPLE 10

Reaction of a Cyclopentene-containing Mixture with Formic Acid

A cyclopentene-containing mixture from a $C_5$ cut of a steam cracker (50 g, 49 wt % of cyclopentene, 0.36 mol, further composition see table in the description) was introduced into a glass autoclave, together with formic acid (99%, 76 g, 1.44 mol) and $BF_3$ etherate (41 mg, 0.36 mol) and, with thorough stirring, heated for 4 hours at 80° C. under intrinsic pressure. The cyclopentene conversion ratio was 92%, as determined by means of quantitative GC analysis, the selectivity for cyclopentyl formate being more than 98%.

Comparative Example 2

Reaction of Cyclohexene with Acetic Acid

Reaction of a cyclohexene/cyclohexane mixture with acetic acid. For purposes of comparison, the starting materials acetic acid and cyclohexene, in the form of a cyclohexene/cyclohexane mixture employed by Wunderly and Sowa, were reacted in a manner similar to Example 10.

Cyclohexene (20.5 g, 0.025 mol), cyclohexane (21 g, 0.025 mol), acetic acid (60 g, 1 mol) and $BF_3$ etherate (2.5 mmol) were introduced into a glass autoclave and heated, with thorough stirring, for four hours at 80° C. After the mixture had cooled down, the selectivity and conversion ratios were determined by quantitative gas chromatography. The cyclohexene conversion ratio was 5% with a selectivity of more than 98%.

EXAMPLE 11

Extraction of Cyclopentyl Formate 500 ml of the output of the reaction from Example 10 were extracted a number of times with 500 ml batches of cyclopentane or n-pentane. The cumulative extraction yields of each extraction step are summarized in the following table.

| | CUMULATIVE EXTRACTION YIELD/% | |
|---|---|---|
| EXTR. STAGE | CYCLOPENTANE | n-PENTANE |
| 1 | 58 | 42 |
| 2 | 84 | 66 |
| 3 | 94 | 81 |
| 4 | 98 | 89 |

In both cases the cyclopentyl formate obtained still contains about 5 wt % of formic acid. The extraction with cyclopentane is distinctly better.

EXAMPLE 12

Transestenification of Cyclopentyl Formate with Methanol to Give Cyclopentanol and Methyl Formate Cyclopentyl formate (0.08 mol) was heated to boiling point with 100 ml of methanol and 0.8 mmol of $NaOCH_3$ while being stirred. The methyl formate formed was distilled off via a distillation column until an overhead temperature of 65° C. (boiling point of methanol) was reached. The yield of cyclopentanol was determined by means of quantitative gas chromatography and was 96%.

We claim:

1. A process for preparing cyclopentyl formates of the formula

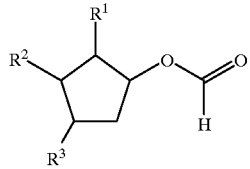

(II)

by reacting cyclopentenes of the formula (I)

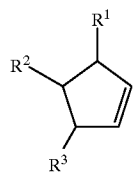

(I)

where $R^1$, $R^2$ and $R^3$, independently of one another, are hydrogen atoms or $C_{1-8}$alkyl, with formic acid in the presence of an acid catalyst selected from Lewis acids of the formula $BX_3$, $AlX_2$, $SnX_4$, $FeX_3$, $MgX_2$, $ZnX_2$, where X is halide or the radical $C_6F_5$, from metal complexes of the formula $(R_3P)MY$, where M is copper, silver or gold, Y is a halide nitrate, sulfate, carboxylate or tosylate, R is $C_{1-12}$alkyl, $C_{6-12}$aryl, $C_{1-12}$O-alkyl or $C_{6-12}$O-aryl, or from Lewis acid or Brönsted acid solid catalysts, wherein the cyclopentyl formates are obtained by extraction of the reaction mixture with cyclopentane and subsequent removal of the cyclopentane.

2. The process of claim 1, wherein the radicals $R^1$, $R^2$ and $R^3$ are hydrogen.

3. The process of claim 1, wherein the cyclopentene of the formula (I) is used in the form of a $C_5$ stream from a cracker or a refinery.

4. The process as claimed in claim 1, wherein the extraction makes use of the cyclopentane present in the $C_5$ stream of a cracker or a refinery.

5. A process for preparing cyclopentanols of the formula (III)

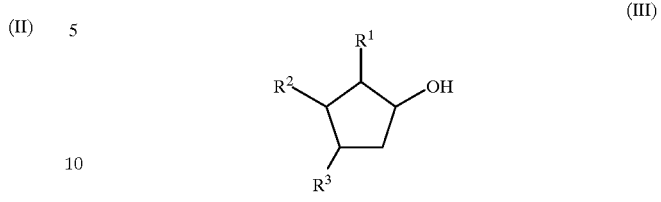

(III)

by reacting the cyclopentyl formates obtained in accordance with the process of claim 1 with a compound of the formula $R^4{}_nXH$, where X is nitrogen and n has the value 2 or X is oxygen and n has the value 1 and $R^4$, possibly independently of each other, is hydrogen, a linear or branched $C_{1-12}$-alkyl or a $C_{7-12}$-aralkyl.

6. The process of claim 5, wherein X is oxygen and $R^4$ is a $C_{1-4}$-akyl.

7. The process as claimed in claim 6, wherein the cyclopentyl formates are transesterified with methanol in the presence of a transesterification catalyst and the methyl formate obtained in the transesterification is hydrolyzed to formic acid and methanol which are recycled into the synthesis.

8. The process of claim 1, wherein $R^1$, $R^2$ and $R^3$ are methyl.

9. The process of claim 1, wherein one or two of the radicals $R^1$, $R^2$ and $R^3$ are methyl and the other radical or radicals are hydrogen.

10. The process of claim 1 wherein the acid catalyst is selected from the group of Lewis acid catalysts $BF_3$, $BF_3$-$OEt_2$ and $ZnCl_2$ or from the complexes $(MeO)_3PCuI$ and $ME_3PAgI$.

* * * * *

UNITED STATES PATENT AND TRADEMARK OFFICE
CERTIFICATE OF CORRECTION

PATENT NO.: 6,093,857

DATED: July 25, 2000

INVENTOR(S): FISCHER et al.

It is certified that error appears in the above-identified patent and that said Letters Patent is hereby corrected as shown below:

Col. 9, claim 4, "as claimed in" should be --of--.

Col. 10, claim 6, line 25, "akyl" should be --alkyl--,.

Col. 10, claim 7, line 26, "as claimed in" should be --of--.

Signed and Sealed this

Seventeenth Day of April, 2001

NICHOLAS P. GODICI

*Attesting Officer*   *Acting Director of the United States Patent and Trademark Office*